United States Patent [19]

Sumimoto et al.

[11] 4,094,642

[45] June 13, 1978

[54] INDICATOR FOR ETHYLENE OXIDE GAS

[75] Inventors: Mitsuhiro Sumimoto, Chiba; Haruo Kohama, Tokyo, both of Japan

[73] Assignee: Dai Nippon Insatsu Kabushiki Kaisha, Tokyo, Japan

[21] Appl. No.: 768,850

[22] Filed: Feb. 15, 1977

[51] Int. Cl.² ............................................. G01N 21/12
[52] U.S. Cl. ............................ 23/254 R; 23/253 TP; 21/DIG. 4; 116/114 AM; 252/408
[58] Field of Search .......... 23/253 TP, 232 R, 254 R; 252/408; 21/DIG. 4; 116/114 AM

[56] References Cited

U.S. PATENT DOCUMENTS

| 3,627,469 | 12/1971 | Cheng ................... 23/253 TP |
| 4,015,937 | 4/1977 | Miyamoto ............. 23/253 TP |

*Primary Examiner*—R.E. Serwin
*Attorney, Agent, or Firm*—Koda and Androlia

[57] ABSTRACT

An indicator composition for ethylene oxide gas comprises 4-(4-nitrobenzyl) pyridine, nitrocellulose, a basic substance, and, optionally, a blue coloring agent.

The indicator composition, when exposed to ethylene oxide gas, changes its color to develop a stable color indication, typically of a green color. The composition can take any shape and form, and is typically applied to a substrate such as paper to form a layer thereon.

19 Claims, 3 Drawing Figures

INDICATOR FOR ETHYLENE OXIDE GAS

BACKGROUND OF THE INVENTION

The present invention relates to an indicator for ethylene oxide gas (hereinafter referred to as "EOG") which is used for sterilization of medical materials and the like.

EOG is extensively used in the sterilization of medical and pharmaceutical materials such as instruments and fabrics, and there has been an urgent demand for the development of a visual indicator for indicating whether or not sterilization by EOG has been completed. However, no satisfactory indicator for EOG has been found heretofore.

There are known various types of indicators for EOG including one which changes its color from yellow to blue when exposed to EOG. However, these known indicators are disadvantageous in that the difference between the colors before and after EOG sterilization is very slight and difficult to distinguish, the resulting color disappearing in a short time after the color change, or the indicators are so sensitive to EOG that a very small amount of EOG can cause a complete color change and it is therefore almost impossible to judge whether or not sufficient EOG sterilization has been effected. Thus, there has been a great need for an improved indicator which is effective for practical use.

The present invention has been developed as a result of our studies for overcoming the above mentioned drawbacks of the known indicators for EOG.

SUMMARY OF THE INVENTION

It is an object of the invention to provide an indicator for EOG which undergoes a remarkable color change when exposed to EOG, whereby the difference in color before and after the EOG sterilization can be easily distinguished.

It is another object of the invention to provide an indicator for EOG by which the resulting color is retained for a long period of time after the EOG sterilization.

It is still another object of the invention to provide an indicator for EOG which reacts with EOG to cause a color change in a quantitative manner thereby to give a measure as to whether or not a sufficient EOG sterilization has been effected.

The foregoing objects have been attained by the indicator composition and structure of this invention.

Thus, according to one aspect of the invention, there is provided an indicator composition for EOG which comprises 4-(4-nitrobenzyl) pyridine, nitrocellulose and a basic substance.

According to another aspect of the invention, there is provided an indicator structure for EOG which comprises a substrate and a layer of indicator composition disposed on the substrate and comprising 4-(4-nitrobenzyl) pyridine, nitrocellulose, and a basic substance.

In a preferred embodiment of the invention, the above-mentioned indicator composition further comprises a blue coloring agent.

It has been known, prior to the present invention, that 4-(4-nitrobenzyl) pyridine, when carried by a filter paper along with a basic substance, functions as an indicator for EOG. The thus obtained indicator, however, undergoes a color change from colorlessness to blue in a time as short as several tens of minutes, and the resulting blue disappears in a short time. In contrast thereto, the indicator composition of this invention is characterized by the inclusion of nitrocellulose in addition to 4-(4-nitrobenzyl) pyridine and a basic substance and, when exposed to EOG, undergoes a stable color change from colorlessness to yellow which does not change or disappear for a long time.

The foregoing objects, other objects as well as the principles of the invention will become more apparent from the following detailed description of the invention together with preferred embodiments thereof and the accompanying drawing.

DETAILED DESCRIPTION

Figure 1:
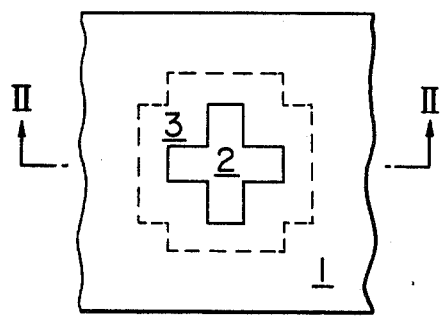
FIG. 1 is a plan view illustrating one example of the indicator structure according to this invention.

The indicator composition for EOG of the invention basically comprises three essential components, namely, 4-(4-nitrobenzyl) pyridine, nitrocellulose, and a basic substance. The composition, basically, may comprise the three components in quantities of any ratio but preferably comprises 1 to 15 parts by weight of 4-(4-nitrobenzyl) pyridine, 12 to 25 parts by weight of nitrocellulose, and 1 to 15 parts by weight of a basic substance in order to give a sufficient color indication after the EOG sterilization. Most preferably, the composition comprises 2 to 10 parts by weight of 4-(4-nitrobenzyl) pyridine, 15 to 20 parts by weight of nitrocellulose, and 2 to 10 parts by weight of a basic substance.

The above stated numerical values in terms of parts by weight for the three components simply define the proportions of the three components in the composition of the present invention, but are also used in this specification as the basis for determining the ranges of the quantities of the optional components which may be used in the indicator composition of the invention along with the above enumerated three essential components.

The basic substance is used to give a basic property as a whole to the composition of the invention. Examples of the basic substance to be used in the present invention include the hydroxides, and normal salts and acidic salts with weak acids of alkaline metals or alkaline earth metals of a pH less than 7 when dissolved in water. Preferable examples of the basic substance are sodium carbonate, sodium bicarbonate, sodium hydroxide, sodium oleate, sodium stearate, and calcium stearate. The basic substances can be used singly or in combination.

The nitrocellulose to be used in the invention preferably has a nitrogen content of 10 to 14%, particularly of 10.7 to 11.5.

The indicator composition preferably comprises a coloring agent, particularly a blue coloring agent. The composition comprising the three essential components is substantially colorless before the exposure to EOG, and changes to yellow after the exposure to EOG. However, while the composition of the invention is ordinarily pointed or applied with an arbitrary pattern on a substrate, the printing or application of the composition is sometimes accompanied by some difficulties in scaling or positioning or judging the printing performance when the composition is colorless. Further, the color change from colorlessness to yellow is not necessarily easy to distinguish by human eye unless it occurs on a colored substrate. For these reasons, it is preferable for the composition of the invention to include a coloring agent and is colored per se.

The coloring agent can be any colored substances as long as they are substantially inert or not harmful to the composition. The preferable coloring agents are commercially available dyestuffs or pigments which produce an easily noticeable initial color before exposure to EOG, and a color sufficiently distinct from the initial color after sufficient exposure to EOG which is developed due to the mixing of the initial color and yellow. The most suitable is a blue coloring agent selected from blue-colored substances including blue dyestuffs and pigments such as phthalocyanine blue, cobalt blue, indathrene blue, and neozapon blue, and mixtures of these blue-colored substances with a small amount of green-colored substances such as phthalocyanine green. These green-colored substances may be used to adjust a coloree tone of the blue coloring agent.

The composition of the invention comprising a blue-coloring agent is easy to distinguish, and changes its color from blue to green after exposure to EOG due to the mixing of blue and yellow. The color change is very sharp and easy to detect, and the resulting green does not become discolored for a long time.

The composition of the invention may further comprise from about 1 to 10 parts by weight of a plasticizer such as 2,2,4-trimethyl-1,3-pentanediol-diisobutylate, castor oil, and citrate esters including acetyl tributyl citrate and ethyl citrate.

The indicator composition of the invention can take any shape and form. For example, the indicator composition can be formed per se into a cake or tablet with relatively high content of the nitro-cellulose acting also as a binder, which cake is thereafter attached to a conatiner or package such as a bag or box for medical materials to be sterilized by EOG. However, the composition is ordinarily prepared first into an ink composition with the addition of a solvent and, optionally, a plasticizer as mentioned above, and then applied onto a desired part of a substrate by a conventional printing method such as gravure printing, silk-screen printing, or brush-painting to form a layer of the indicator composition with a desired pattern such as a cross or the word "STERILIZED" on the part of the substrate after the evaporation of the solvent.

As the solvent for this purpose, a conventional organic solvent such as ethyl acetate, toluene, isopropyl alcohol, methyl ethyl ketone, methyl cellosolve, benzyl alcohol or the like is used ordinarily in a quantity of 40 to 80 parts by weight, particularly about 60 parts by weight on the basis specified hereinabove.

In the ink composition thus prepared, nitrocellulose also functions as a binder. It has been found that when a conventional binder for an ink composition such as a polyester, a vinyl chloride/vinyl acetate copolymer, chlorinated polypropylene, butyral resin, cyclized rubber or a polyamide is used instead of nitrocellulose in the composition of the invention, the resulting composition is utterly different from the composition of the inventin and can develop only a light blue color after exposure to EOG in the absence of a blue coloring agent, and the resultant blue color disappears in a short time. Thus such an indicator composition containing no nitrocellulose is not applicable to practical use at al.

In the preparation of the ink composition according to the invention, it is preferable in some cases to first disperse the components except for nitro-cellulose, i.e., 4-(4-nitrobenzyl) pyridine, a basic substance, and, optionally, a coloring agent, in a solution of, for example, polyvinyl alcohol, then to evaporate off the solvent after mixing, and to pulverize the resulting solid to form a fine-powder of micro-capsules wherein the components except for nitro-cellulose are encapsulated within polyvinyl alcohol resin.

An ink composition is prepared by mixing the micro-capsules thus obtained, nitro-cellulose, and a conventional solvent as mentioned above. As a resin for forming micro-capsules for this purpose, a gas-permeable thermoplastic resin such as polyvinyl chloride, polyesters, polymethylmethacrylate, or polyvinylidene chloride, can be used instead of polyvinly alcohol. When this ink composition comprising micro-capsules is applied with proper selection of the resin for the micro-capsules and the wall thickness of the capsules, the penetration of EOG can be controlled. Accordingly, an indicator thus prepared can effectively function as a quantitatively responsive indicator for EOG under a variety of sterilization conditions.

A substrate to be coated or marked with the indicator composition of the invention can be of any of a number of materials including natural or synthetic paper, plastic plate, or film, metal plate, and the like, and can be a portion of a container or package for the materials to be sterilized such as a bag, a box or the like, or a piece of an article such as a card which is to be attached to the container or package with adhesive, card holder, or the like.

The indicator structure thus obtained comprises a substrate and a layer of the indicator composition of the invention disposed at least partially on the substrate. The quantity of the indicator layer ordinarily ranges from 1 to 20 g-solid/m$^2$ of the indicator pattern on the substrate.

It is sometimes advantageous to overcoat the layer of the indicator composition with a resinous overcoating layer. The material for the overcoating layer can be any of gaspermeable film-forming resins capable of controlling the permeation of EOG therethrough by adjusting their film thickness including thermoplastic resins such as polyesters, polyamides, polyvinyl choloride, vinyl chloride/vinyl acetate copolymers, acrylic resin, polyvinylidene chloride, polyethylene, and polypropylene, and thermosetting resins such as unsaturated polyester resins, and polyurethane resins.

When such an overcoating layer is provided over the layer of the indicator, the following advantages are obtained.

(1) The time for the color change can be controlled since the permeation of EOG during the sterilization can be controlled by proper selection of the overcoating resin and the thickness of the layer. Thus, an indicator structure quantitatively indicating the degree of the sterilization can be provided.

(2) The deterioration of the indicator composition due to light is decreased by the protecting effect of the overcoating layer. In this regard, a resin of excellent lightresistance such as an acrylic resin or polyvinyl chloride is particularly preferred as an overcoating resin.

(3) The developed color resulting from the sterilization can be retained for a longer time without discoloration.

Such an overcoating layer is provided over the layer of the indicator composition by any of the conventional methods. For example, a film of the overcoating resin prepared in advance is applied with adhesive or by heat-sealing, or a solution or a dispersion of the overcoating resin is applied over the layer of the indicator composition on the substrate followed by evaporation of the medium to form a layer of the overcoating resin. The quantity of the overcoating resin to be applied in terms of g-solid/m² of the overcoating area ranges from 1 to 20.

Figure 2:
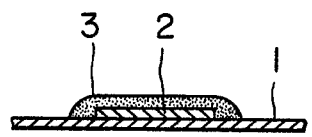
FIG. 2 is a section taken along the plane indicated by line II—II in FIG. 1 as viewed in the arrow direction.

The indicator structure thus obtained has a structure as shown in FIG. 2 which is a partial view in section taken along line II—II of FIG. 1, and comprises a substrate 1, a layer of the indicator composition 2 disposed on the substrate 1 and a resinous overcoating layer 3 over the layer 2. The layer 2 can be of any planar pattern e.g., a pattern of a cross as shown in FIG. 1.

Figure 3:
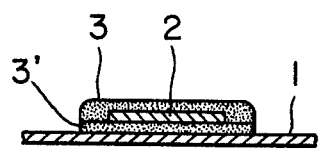
FIG. 3 is a section similar to FIG. 2 showing another example of the indicator structure of the invention.

When the substrate 1 is made of a gas-permeable material such as paper, an undercoating layer 3' as shown in FIG. 3 may further be inserted between the substrate 1 and the layer of indicator composition 1 according to necessity in order to suppress the permeation of EOG through the substrate and to obtain an even better quantitative indication of the degree of sterilization. The material for the undercoating layer can be the same as that for the overcoating layer as described hereinabove.

Such an undercoating layer can also be effectively provided on a substrate of a hardly printable material such as metal plate or foil in order to give an appropriate printability to the substrate.

The indicator composition or structure according to the invention, as a part of a container or package for materials to be sterilized or after having been attached to the container or the materials to be sterilized per se, is subjected to EOG sterilization. While pure EOG can be used as a sterilization gas, it is preferable to dilute EOG with an inert gas such as Freon and carbon dioxide to form and use a sterilization gas mixture containing EOG at a concentration of about 10 to 30% since the explosiveness of EOG can be sufficiently suppressed thereby.

In order to indicate more fully the nature and utility of the invention, the following actual examples of practice are presented, it being understood that these examples are not forth as illustrative only and are not intended to limit the scope of the invention.

EXAMPLE 1

On a gas-permeable paper portion of a packaging bag for gas sterilization, an indicator ink composition comprising 4 parts by weight of 4-(4-nitrobenzyl) pyridine, 18 parts by weight of nitrocellulose, 5 parts by weight of sodium carbonate, 2 part by weight of phthalocyanine blue, 8 parts by weight of 2,2,4-trimethyl-3,3-pentanedioldiisobutylate, and 63 parts by weight of ethyl acetate as a solvent was applied in a pattern of a cross as shown in FIG. 1 by gravure process and thereafter dried. The packaging bag with the indicator for EOG applied thereon was exposed to a sterilization gas mixture of 20% by volume of EOG and 80% by volume of carbon dioxide at a pressure of 1.0 atm. and a temperature of 50° C for 5 hours. The indicator which had been blue at first began to change its color to green at a time of about 30 minutes and completely turned green in about 1 hour. The resultant green color did not undergo any discoloration whatsoever even after 3 months from the finish of the sterilization.

EXAMPLE 2

The indicator ink composition as used in EXAMPLE 1 was applied in a pattern of a cross at a rate of 4g-solid/m² onto a sterile paper of 60 g/m² constituting a bag and was dried thereafter. A toluene solution of an acrylic resin with a solid concentration of about 20 to 25% by weight was applied over the cross pattern of the indicator composition at a rate of 3g-solid/m² and dried to prepare a bag with the EOG indicator applied thereon.

Three groups of the bags thus prepared were exposed to a gas mixture of EOG and Freon in a volume ratio of 12:88 at a relative humidity of about 60% respectively at 40° C, 50° C and 60° C. The initial blue color of the indicators completely turned green in about 4 hours at 40° C, about 3 hours at 50° C, and about 2 hours at 60° C, respectively.

During the sterilization operation, filter paper strips each inoculated with about $10^6$ Bacillus subtilis were respectively inserted in the bags in order to check the effect of the above three sterilization runs. As a result, it was found that all of the bacillic were killed by each sterilization run.

It was further found that the provision of an overcoating layer could prolong the time required for the color change, and the degree of the sterilization could be correlated to some extent with the degree of the color change, whereby the control of the sterilization process was made easier in comparison with the case of no overcoating layer. Further, the resultant green color did not change at all even after 4 months from the finish of the sterilization, and the provision of an overcoating layer was found effective also in this respect.

We claim:

1. An indicator composition for ethylene oxide gas which comprises 4-(4-nitrobenzyl)-pyridine, nitrocellulose, and a basic substance.

2. The indicator composition according to claim 1 which further comprises a coloring agent.

3. The indicator composition according to claim 2 in which said coloring agent is a blue coloring agent.

4. The indicator composition according to claim 1 which comprises 1 to 15 parts by weight of 4-(4-nitrobenzyl) pyridine, 12 to 25 parts by weight of nitrocellulose, and 1 to 15 parts by weight of the basic substance.

5. The indicator composition according to claim 4 which further comprises 1 to 10 parts by weight of a blue coloring agent.

6. The indicator composition according to claim 5 which further comprises 40 to 80 parts by weight of an organic solvent.

7. The indicator composition according to claim 3 in which said 4-(4-nitrobenzyl) pyridine, basic substance and blue coloring agent are encapsuled in resinous microcapsules and dispersed in said nitrocellulose.

8. An indicator composition for ethylene oxide gas which comprises 2 to 10 parts by weight of 4-(4-nitrobenzyl)-pyridine, 15 to 20 parts by weight of nitrocellulose, 2 to 10 parts by weight of a basic substance, and 1 to 10 parts by weight of a blue coloring agent.

9. The indicator composition according to claim 8 in which said basic substance is selected from the group consisting of sodium carbonate, sodium bicarbonate, sodium hydroxide, sodium oleate, sodium stearate, and calcium stearate, and said blue coloring agent is selected from the group consisting of phthalo-cyanine blue, cobalt blue, indathrene blue, and neozapon blue.

10. The indicator composition according to claim 5 which further comprises 1 to 10 parts by weight of a plasticizer selected from the group consisting of 2,2,4-trimethyl-1,3-pentanediol-dissobutylate, castor oil, acetyl tributyl citrate and ethyl citrate.

11. An indicator structure for ethylene oxide gas which comprises a substrate and a layer of indicator composition disposed on the substrate and comprising 4-(4-nitrobenzyl)-pyridine, nitrocellulose, a basic substance, and a blue coloring agent.

12. The indicator structure according to claim 11 which further comprises a resinous overcoating layer disposed over said layer of indicator composition.

13. The indicator structure according to claim 11 which further comprises a resinous undercoating layer interposed between said substrate and said layer of indicator composition.

14. The indicator structure according to claim 11 in which said layer of indicator composition comprises 2 to 10 parts by weight of 4-(4-nitrobenzyl)-pyridine, 15 to 20 parts by weight of nitrocellulose, 2 to 10 parts by weight of a basic substance, and 1 to 10 parts by weight of a blue coloring agent.

15. The indicator structure according to claim 12 in which said resinous overcoating layer is made of a thermoplastic resin selected from the group consisting of polyesters, polyamides, polyvinyl chloride, vinyl chloride/vinyl acetate copolymer, acrylic resins, polyvinylidene chloride, polyethylene, and polypropylene.

16. The indicator structure according to claim 12 in which said resinous overcoating layer is made of a thermosetting resin selected from the group consisting of unsaturated polyester resins and polyurethane resins.

17. The indicator structure according to claim 11 in which the quantity of the indicator composition on the substrate ranges from 1 to 20g-solid/m$^2$ of the area of the indicator composition.

18. The indicator structure according to claim 12 in which the quantity of the overcoating resin ranges from 1 to 20 g-solid/m$^2$ of the overcoating area.

19. The indicator structure according to claim 11 in which the substrate is a part of a structure for containing a product to be exposed to ethylene oxide gas to be indicated by the indicator composition.

* * * * *